United States Patent
Matsuzaki et al.

(10) Patent No.: US 10,085,707 B2
(45) Date of Patent: Oct. 2, 2018

(54) MEDICAL IMAGE INFORMATION SYSTEM, MEDICAL IMAGE INFORMATION PROCESSING METHOD, AND PROGRAM

(71) Applicant: HITACHI, LTD., Tokyo (JP)

(72) Inventors: Kazuki Matsuzaki, Tokyo (JP); Yuuichi Morimoto, Tokyo (JP); Wataru Takeuchi, Tokyo (JP); Kikuo Umegaki, Sapporo (JP); Tohru Shiga, Sapporo (JP); Koichi Yasuda, Sapporo (JP)

(73) Assignee: Hitachi, Ltd., Tokyo (JP)

( * ) Notice: Subject to any disclaimer, the term of this patent is extended or adjusted under 35 U.S.C. 154(b) by 50 days.

(21) Appl. No.: 15/305,458

(22) PCT Filed: Mar. 30, 2015

(86) PCT No.: PCT/JP2015/059867
§ 371 (c)(1),
(2) Date: Oct. 20, 2016

(87) PCT Pub. No.: WO2015/163089
PCT Pub. Date: Oct. 29, 2015

(65) Prior Publication Data
US 2017/0042495 A1    Feb. 16, 2017

(30) Foreign Application Priority Data
Apr. 24, 2014   (JP) .................................. 2014-090139

(51) Int. Cl.
*G06K 9/00*    (2006.01)
*A61B 6/00*    (2006.01)
(Continued)

(52) U.S. Cl.
CPC .............. *A61B 6/5217* (2013.01); *A61B 5/00* (2013.01); *A61B 5/055* (2013.01); *A61B 6/032* (2013.01);
(Continued)

(58) Field of Classification Search
CPC ....... G06T 7/11; G06T 7/162; G06T 2200/04; G06T 2207/20072; G06T 2210/41
See application file for complete search history.

(56) References Cited

U.S. PATENT DOCUMENTS

2009/0024615 A1* 1/2009 Pedro ................ G06F 17/30734
2009/0279758 A1* 11/2009 Dikici ....................... G06T 7/11
                                                                           382/128
(Continued)

FOREIGN PATENT DOCUMENTS

| JP | 2007-044488 A | 2/2007 |
| JP | 2010-017421 A | 1/2010 |

OTHER PUBLICATIONS

Daisuke Kobyashi, "Tree-Graph Representation of Main-Sub Trunk Type 3D Blood Vessels by Route-Based Approach", The Transaction of the Institute of Electronics, Information and Communication Engineers, Apr. 1, 2009, vol. J92-D, No. 4, p. 511-520.

(Continued)

*Primary Examiner* — Li Liu
(74) *Attorney, Agent, or Firm* — Mattingly & Malur, PC

(57) ABSTRACT

The present invention correlates information, to be processed, about an organ and/or a disease, etc., obtained from a medical image and anatomical/functional medical knowledge information, and enables the information obtained from the medial image to be effectively utilized in medical examination and treatment processes. In a medical image information system (101), an image processing unit (103) processes an image, a graph model creation unit (104)
(Continued)

creates a graph data model from the information obtained from the image, a graph data model processing unit (106) acquires a graph data model based on anatomical/functional medical knowledge, compares with each other and integrates the graph data models and stores an integrated graph data model, and a display processing unit (110) displays the integrated graph data model, whereby the effective use of information obtained from the image is made possible.

16 Claims, 13 Drawing Sheets

(51) Int. Cl.
| | | |
|---|---|---|
| G16H 50/50 | (2018.01) | |
| A61B 5/00 | (2006.01) | |
| G06Q 50/24 | (2012.01) | |
| A61B 5/055 | (2006.01) | |
| A61B 6/03 | (2006.01) | |
| G06F 17/30 | (2006.01) | |
| G06F 19/00 | (2018.01) | |
| G06K 9/62 | (2006.01) | |
| G06T 7/00 | (2017.01) | |
| G06T 11/20 | (2006.01) | |
| G06T 7/11 | (2017.01) | |
| G06K 9/46 | (2006.01) | |
| G06K 9/68 | (2006.01) | |
| G06T 7/162 | (2017.01) | |

(52) U.S. Cl.
CPC .............. *A61B 6/037* (2013.01); *A61B 6/501* (2013.01); *A61B 6/503* (2013.01); *A61B 6/504* (2013.01); *G06F 17/3028* (2013.01); *G06F 17/30256* (2013.01); *G06F 19/321* (2013.01); *G06F 19/325* (2013.01); *G06F 19/3437* (2013.01); *G06K 9/469* (2013.01); *G06K 9/6256* (2013.01); *G06K 9/6892* (2013.01); *G06Q 50/24* (2013.01); *G06T 7/0012* (2013.01); *G06T 7/11* (2017.01); *G06T 7/162* (2017.01); *G06T 11/206* (2013.01); *G16H 50/50* (2018.01); *G06T 2207/10072* (2013.01); *G06T 2207/10081* (2013.01); *G06T 2207/10088* (2013.01); *G06T 2207/10104* (2013.01); *G06T 2207/10108* (2013.01); *G06T 2207/20072* (2013.01); *G06T 2207/20161* (2013.01); *G06T 2207/30016* (2013.01); *G06T 2207/30048* (2013.01); *G06T 2207/30056* (2013.01); *G06T 2207/30096* (2013.01); *G06T 2207/30101* (2013.01)

(56) References Cited

U.S. PATENT DOCUMENTS

| | | | |
|---|---|---|---|
| 2014/0343965 A1* | 11/2014 | Miyoshi | G06F 19/322 705/3 |
| 2015/0193943 A1* | 7/2015 | Li | G06T 7/0093 382/131 |
| 2016/0027342 A1* | 1/2016 | Ben-Haim | A61B 5/4035 434/272 |
| 2016/0048608 A1* | 2/2016 | Frieden | G06F 17/30958 707/722 |

OTHER PUBLICATIONS

Kensaku Mori, et al., "Automated Anatomical Labeling of the Bronchial Branch and Its Application to the Virtual Bronchoscopy System", IEEE Transactions on Medical Imaging, Feb. 2000, vol. 19, No. 2, p. 103-111.

International Search Report of PCT/JP2015/059867 dated Jun. 9, 2015.

International Preliminary Report on Patentability received in corresponding International Application No. PCT/JP2015/059867 dated Nov. 3, 2016.

* cited by examiner

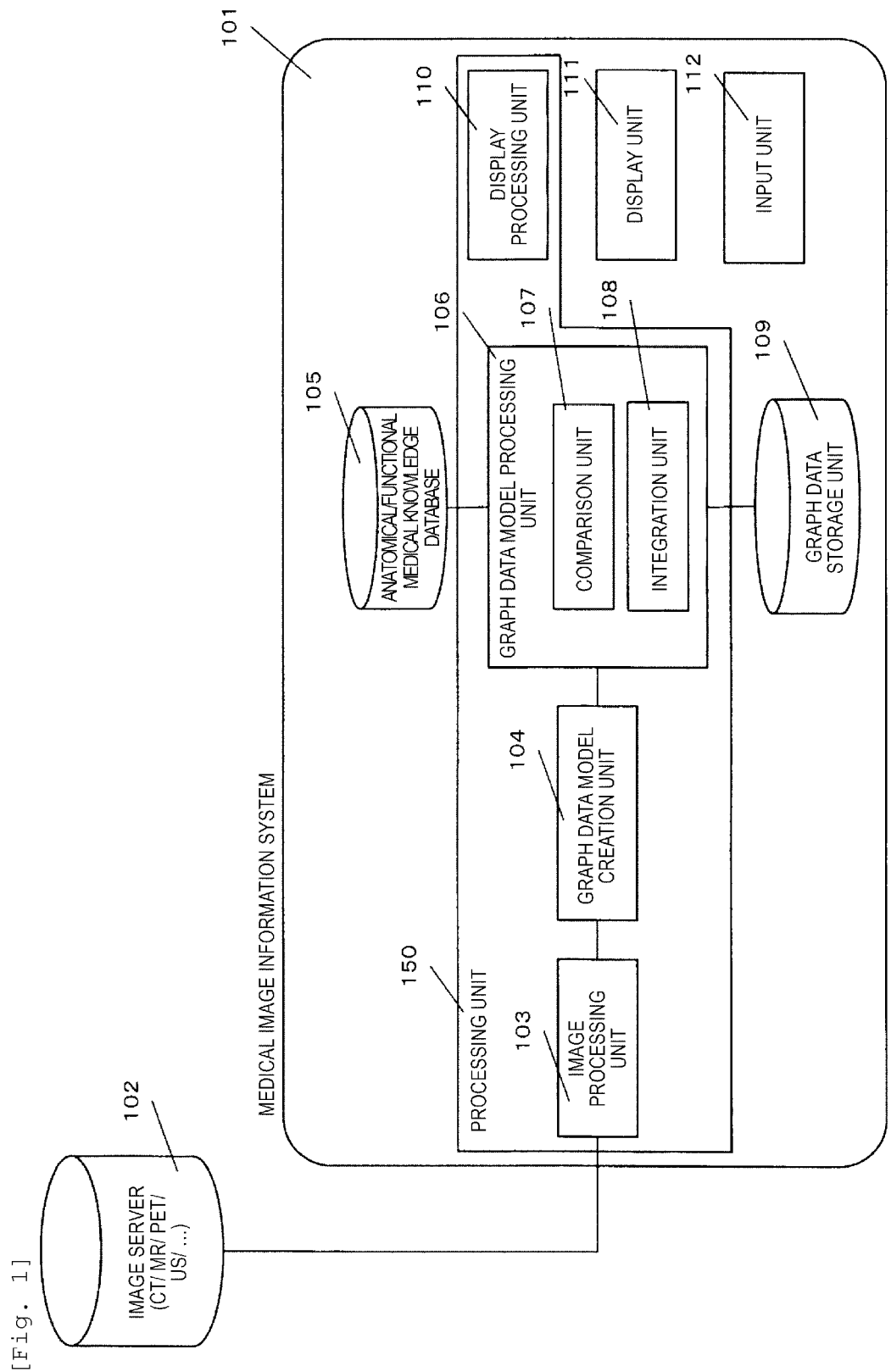

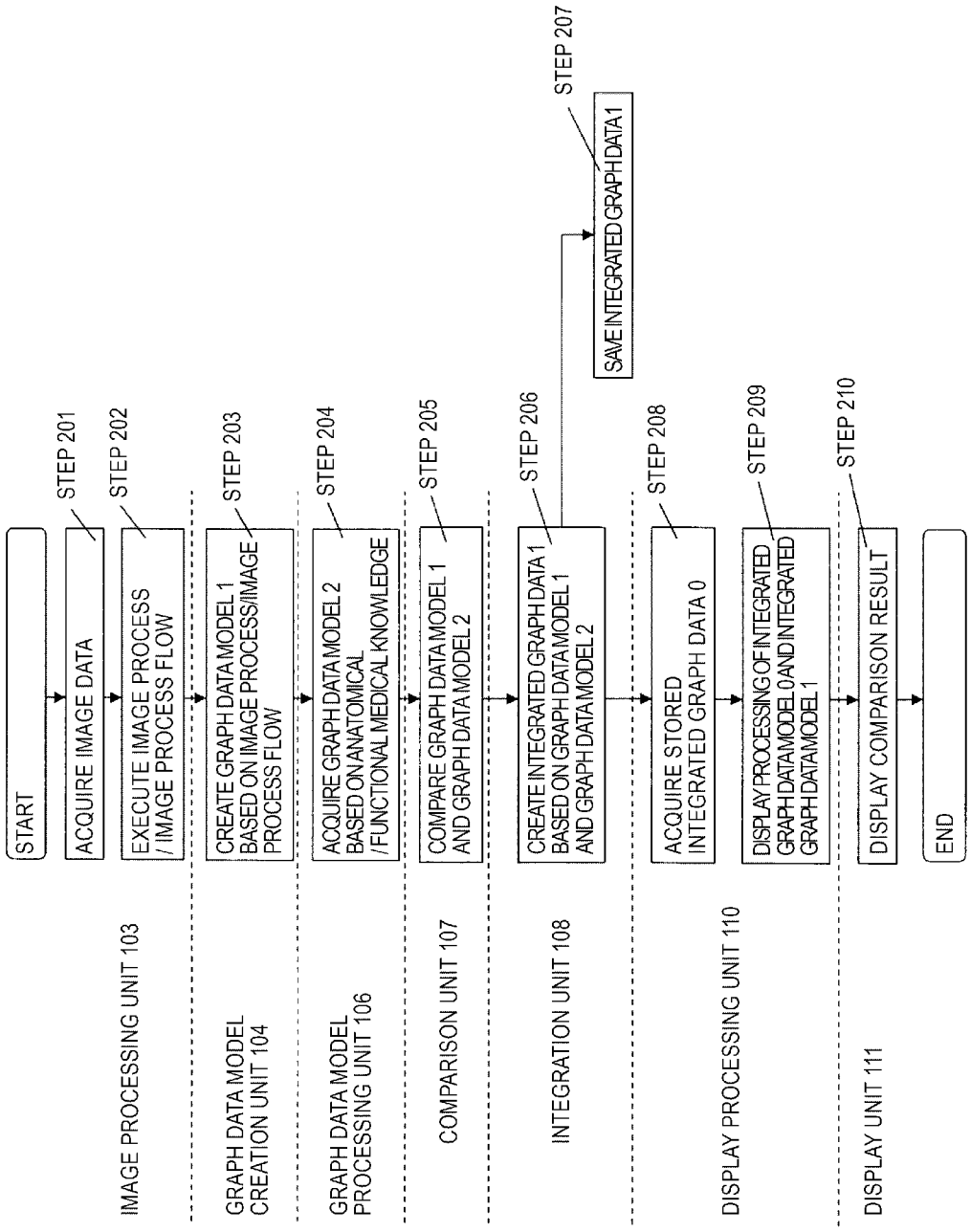
[Fig. 2]

[Fig. 3]
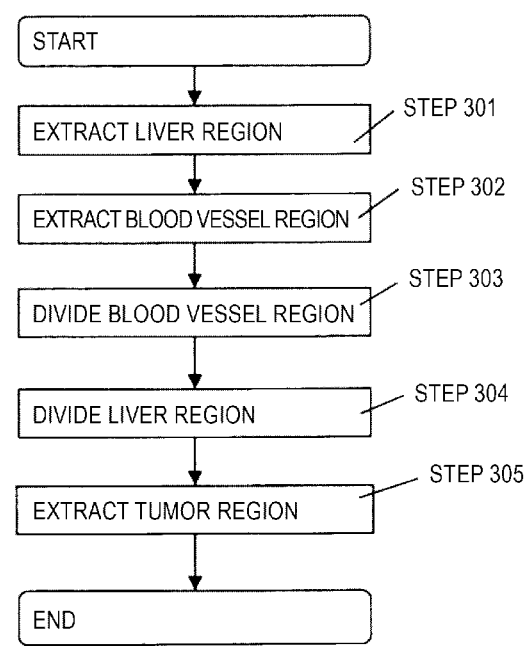

[Fig. 4]
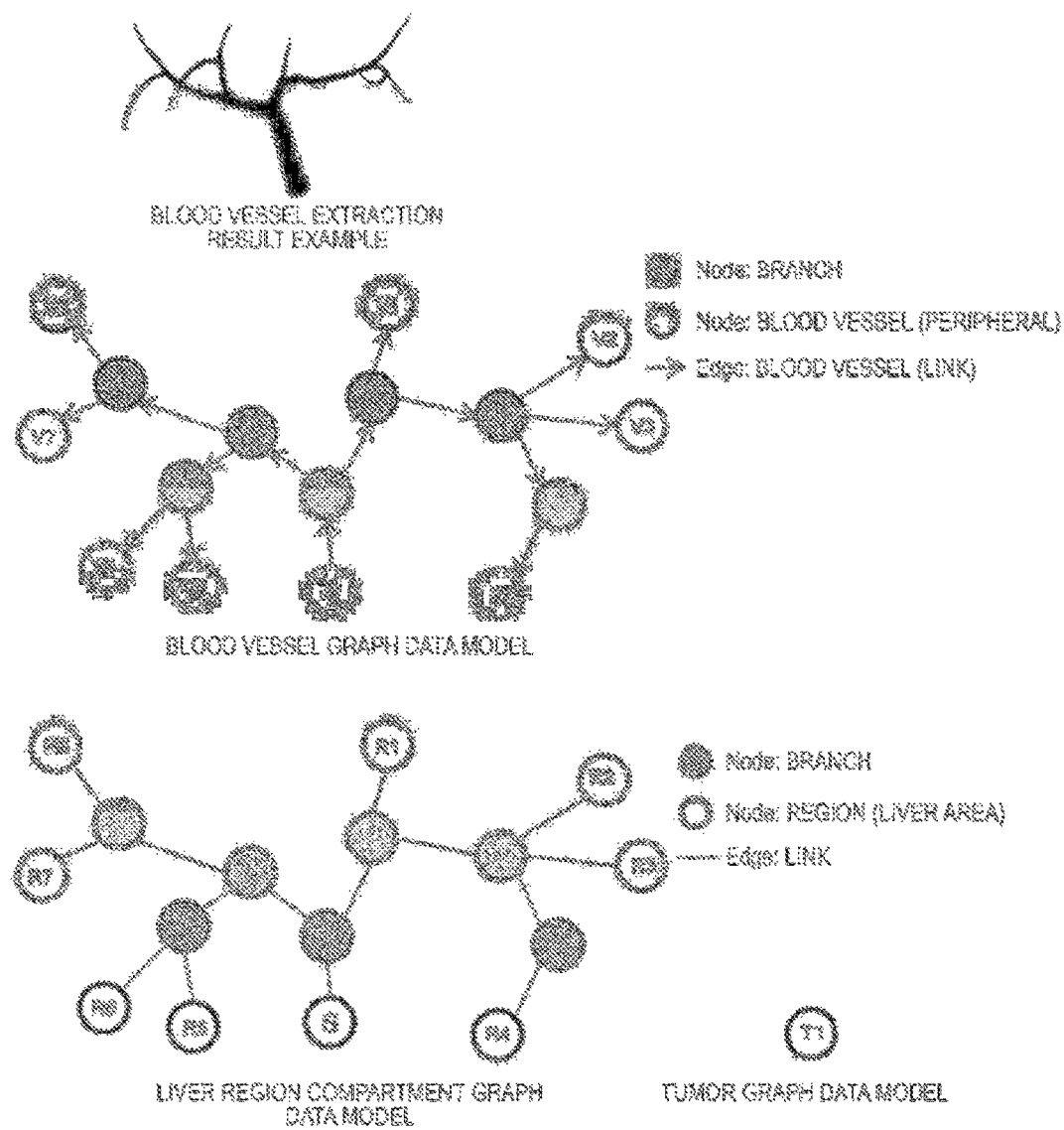

[Fig. 5]
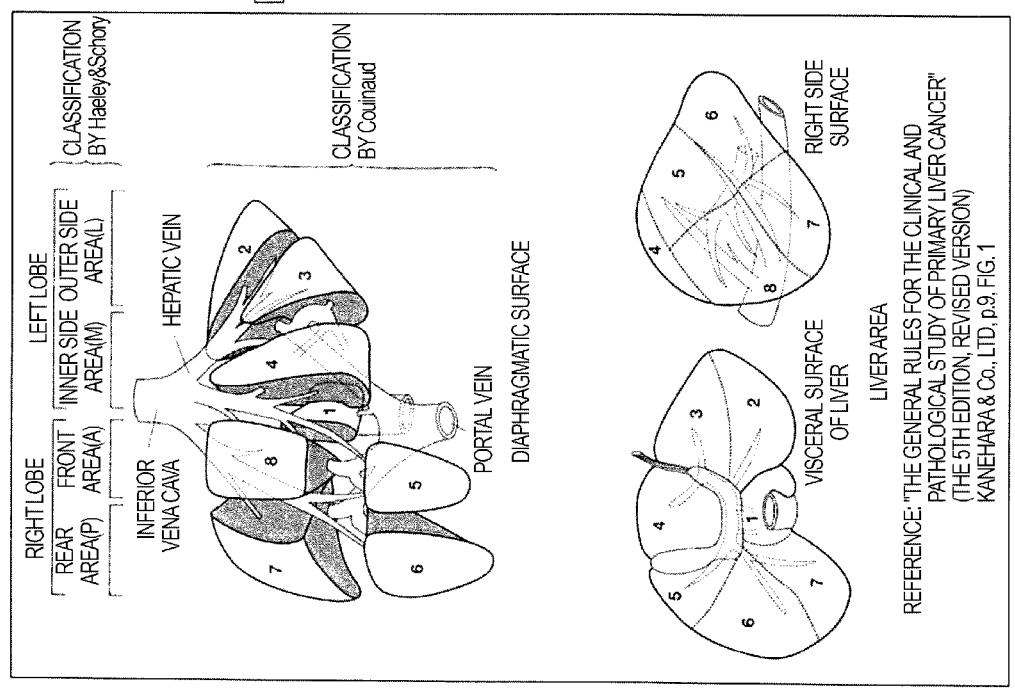

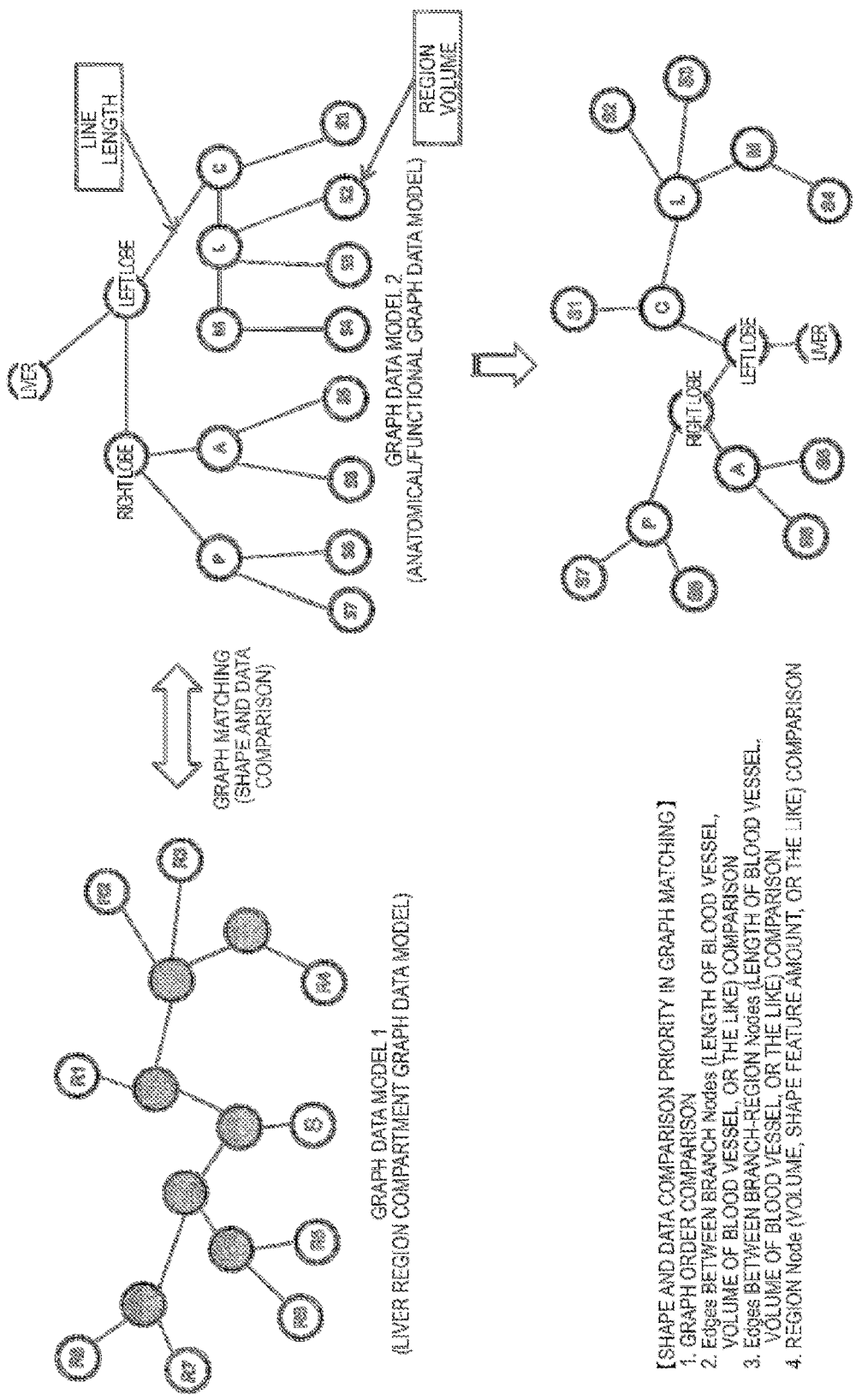

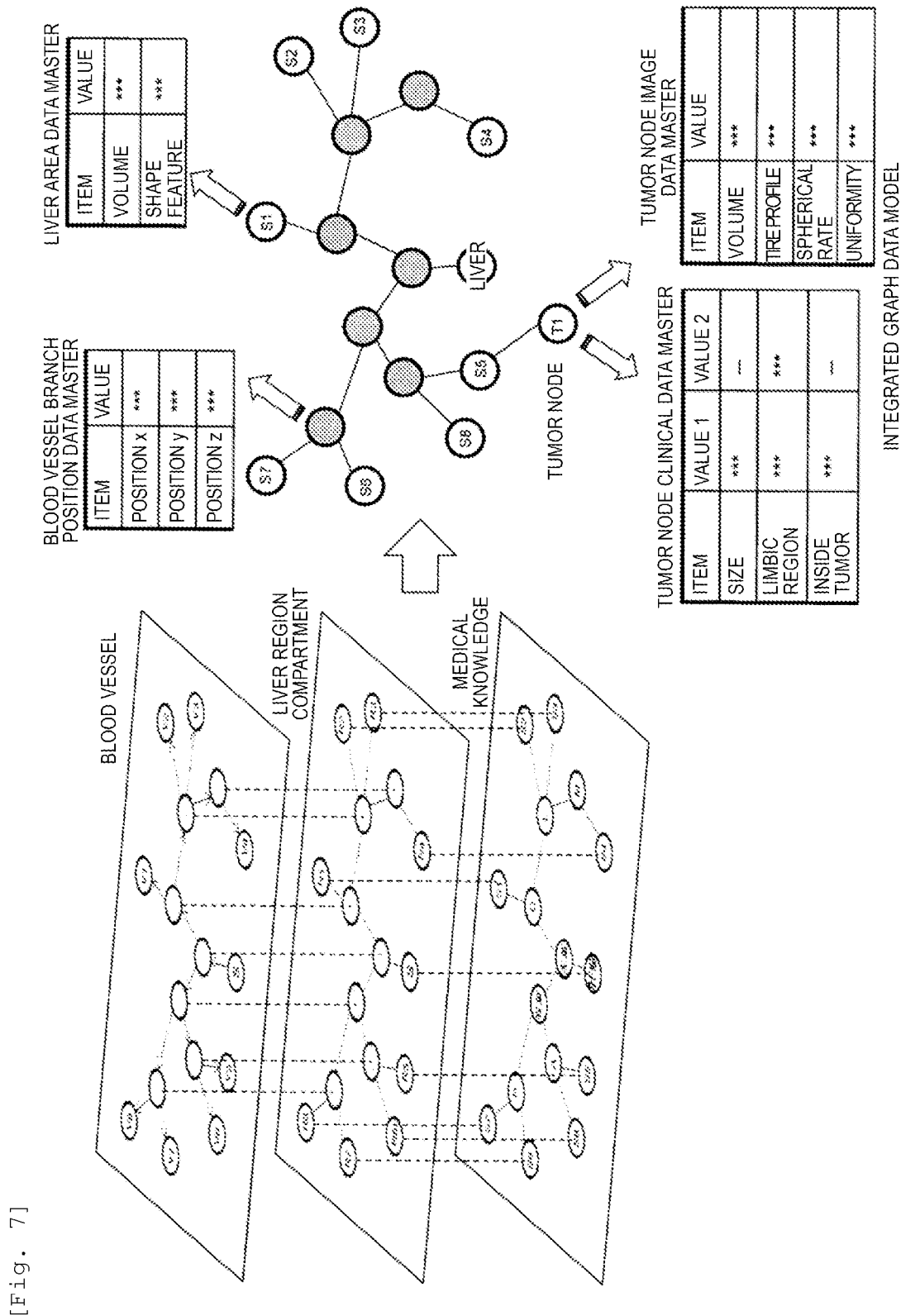
[Fig. 7]

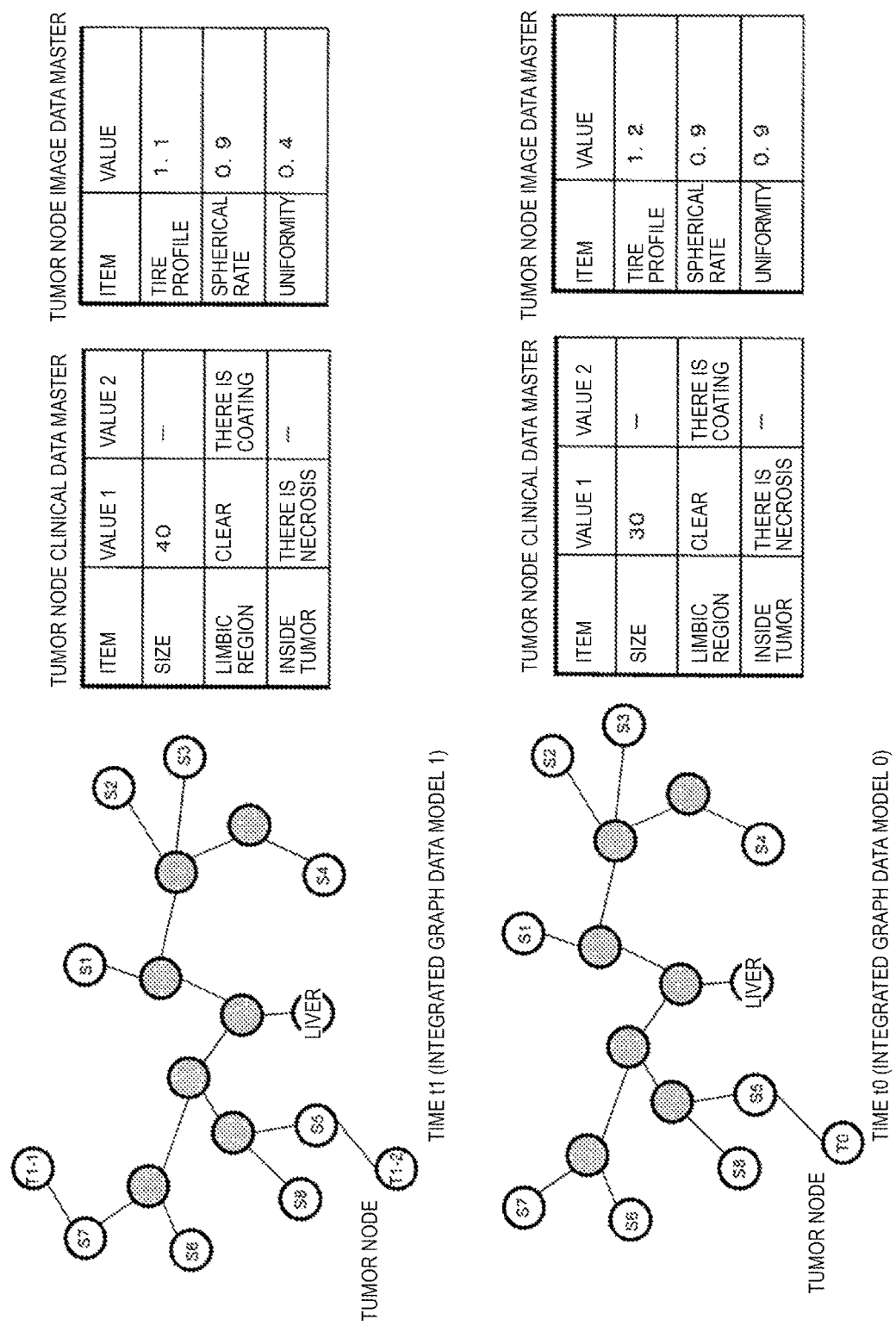
[Fig. 8]

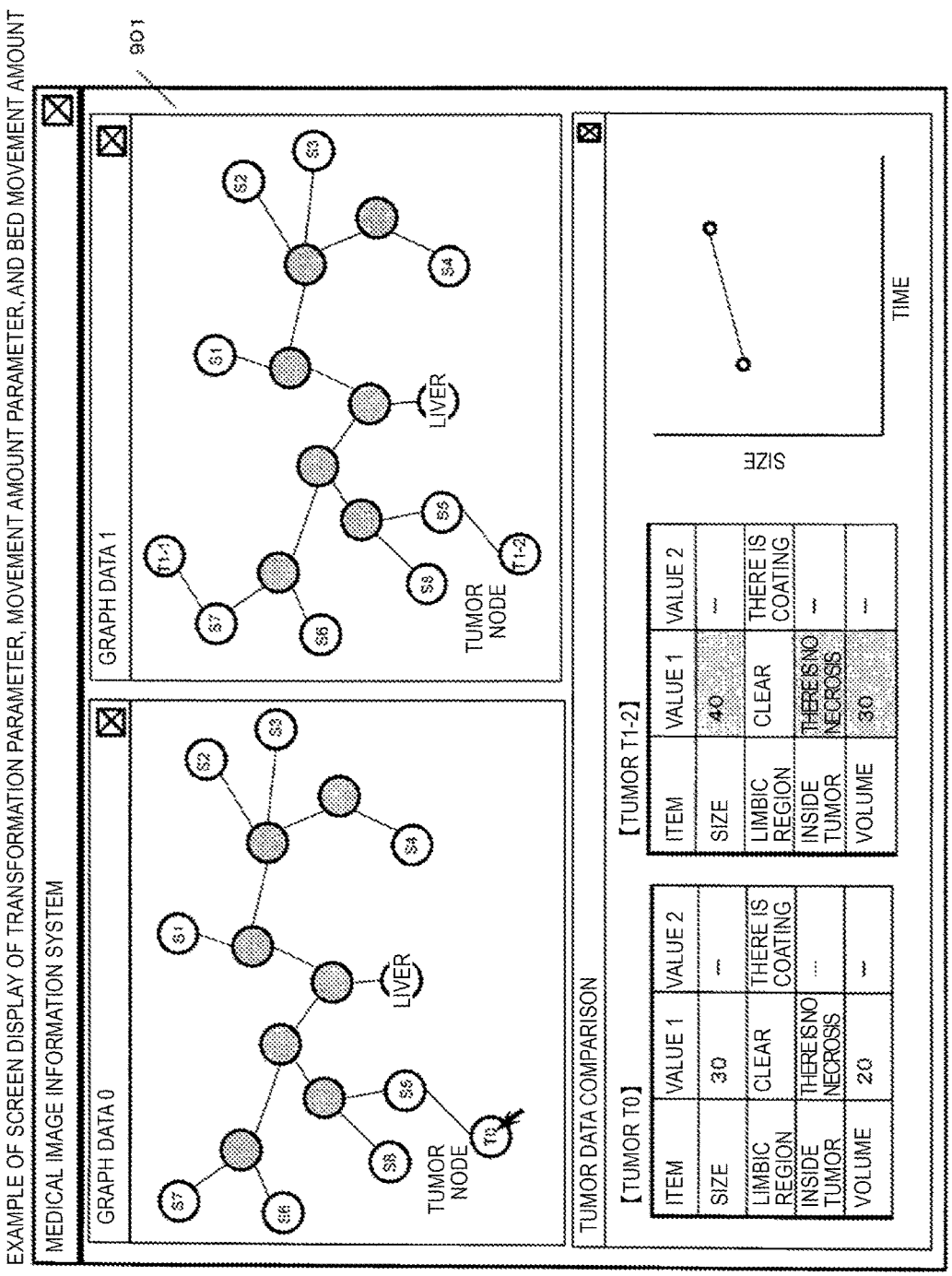

[Fig. 10]
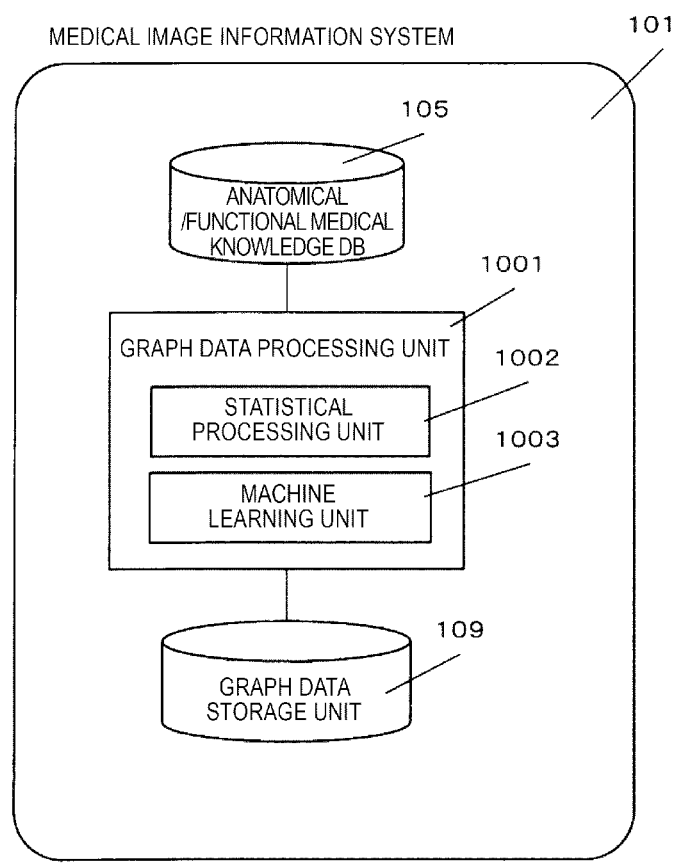

[Fig. 11]
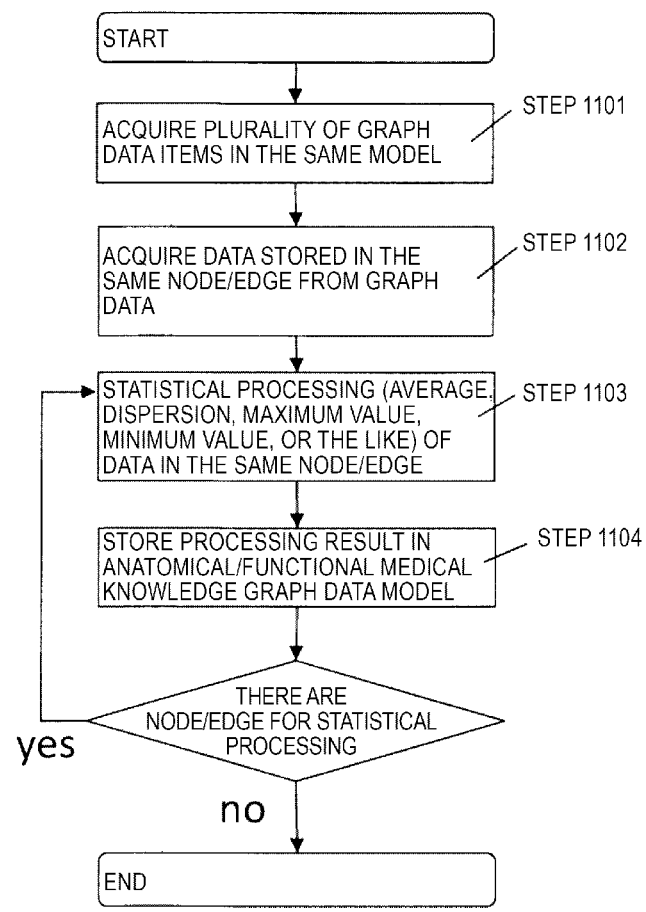

[Fig. 12]
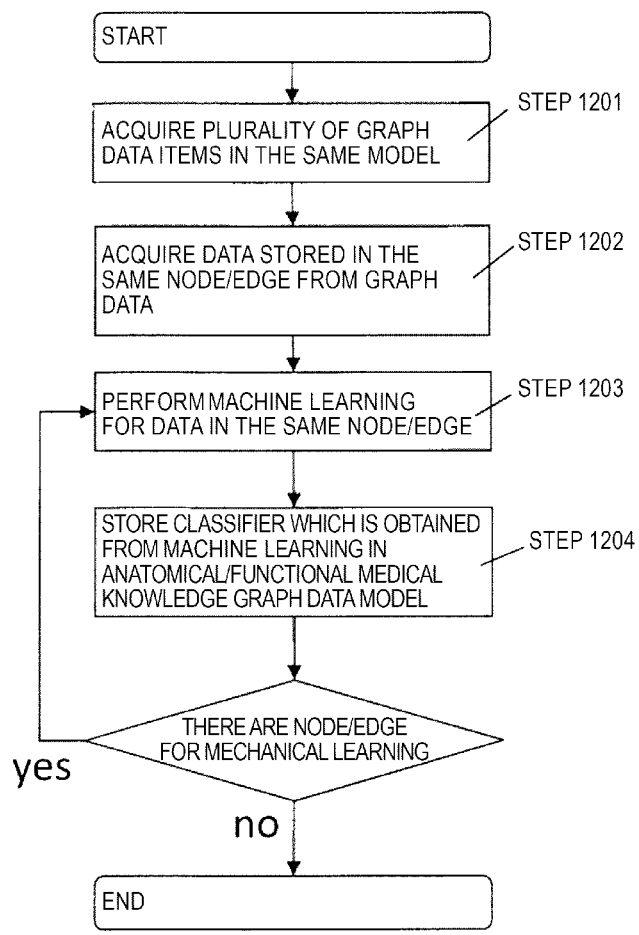

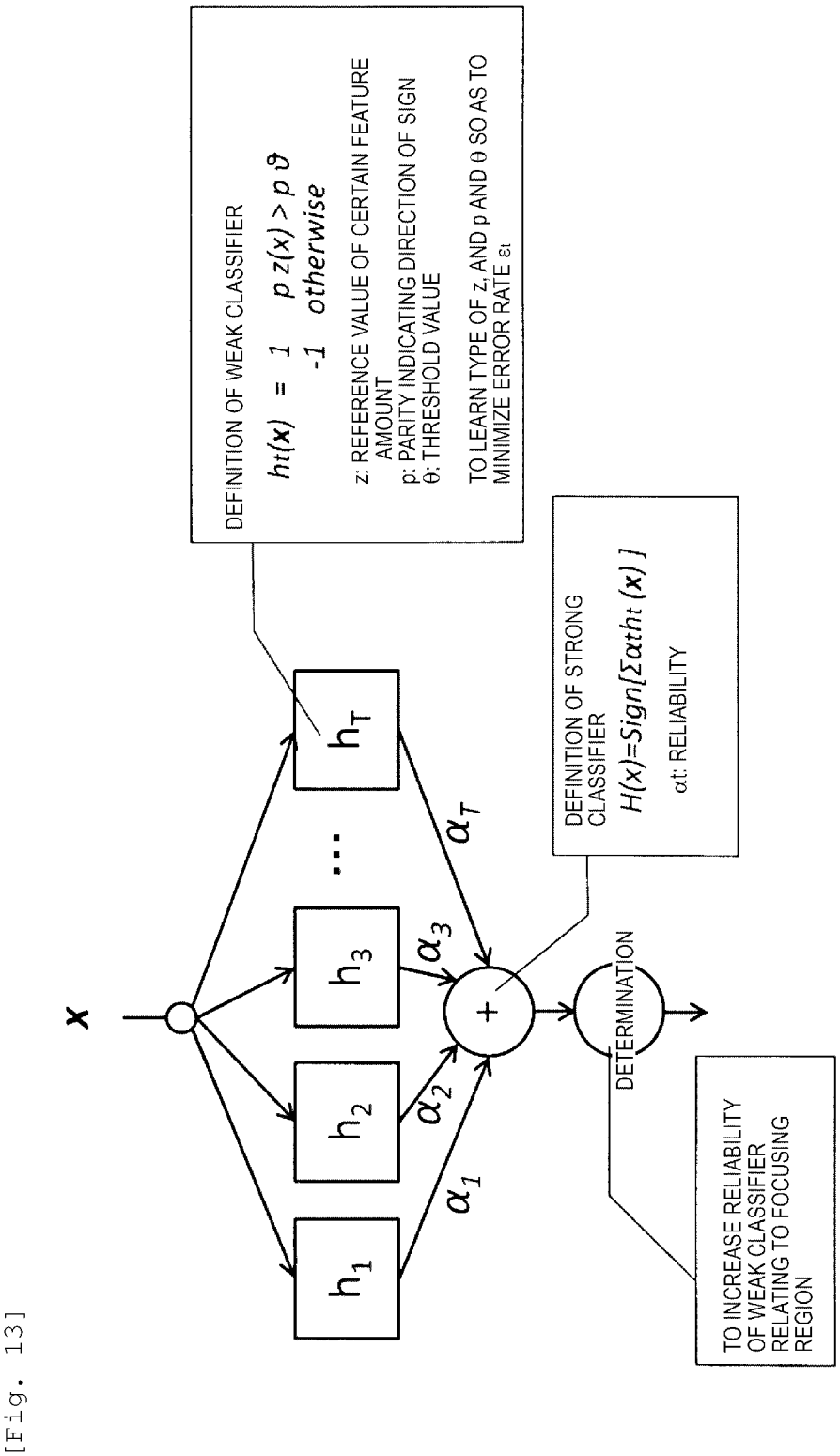
[Fig. 13]

MEDICAL IMAGE INFORMATION SYSTEM, MEDICAL IMAGE INFORMATION PROCESSING METHOD, AND PROGRAM

TECHNICAL FIELD

The present invention relates to a medical image information system, a medical image information processing method, and a program, and in particular, a medical image information system, a medical image information processing method, and a program for obtaining information, to be processed, about a body part and/or a disease, or the like, from a medical image, image processing, and accumulating the information to be effectively utilized.

BACKGROUND ART

Medical image diagnosis allows body information to be obtained noninvasively and thus has been widely performed in recent years. Three-dimensional images obtained by various types of image diagnosis apparatuses such as x-ray computer tomography (CT) apparatuses, magnetic resonance imaging (MRI) apparatuses, positron emission tomography (PET) apparatuses, and single photon emission computed tomography (SPECT) apparatuses have been used in diagnosis or follow-up.

An image obtained by such a medical image diagnosis apparatus is viewed for reading, simply and can also obtain various information items through an image process. For example, in the X-ray CT apparatus, since a volume image having a high spatial resolution can be obtained, images of a body part, a blood vessel, or the like are extracted by a segmentation technology, and it is possible to three-dimensional visualization these images by a volume rendering method. Furthermore, the images can be visualized simply, and it is possible to quantitatively evaluate the images by extracting a disease site such as a tumor using various image process algorithms to obtain a maximum diameter or a volume of the images. In the related art, as a system for aiding a medical image diagnosis, a computer aided diagnosis (CAD) is proposed. When the CAD is finely functional classified, the CAD is divided into a computer aided detection (CADe) and a computer aided diagnosis (CADx). In the CADe, a candidate position in which a focus of disease is present on an image is automatically detected by a computer. The CADe has a function for marking the position and aids in pointing out the lesion. On the other hand, the CADx has a function for output a numerical value of physical characteristics relating to the lesion candidate (maximum diameter, volume, or the like), a malignancy differentiation, or data or numerical value of the degree of progress of the lesion in addition to the CADe function. The CADx outputs qualitative and quantitative data of the lesion to aid the diagnosis. Among them, a CADe system for a lung cancer and breast cancer has been commercialized, and its importance increases.

On the other hand, the medical image is used in not only the diagnosis but also the treatment. Specifically, the importance of the image in a radiation treatment increases. The radiation treatment is mainly subjected in four steps a diagnosis, a treatment plane, a treatment, and a follow-up. An image or an image process technology is used in each step. In bed positioning that is an important process in the treatment, in order to obtain positioning with higher accuracy than a two-dimensional image which is performed in the related art, an image guided radiation therapy (IGRT) using a three-dimensional image is performed.

The information obtained from such a medical image and an image process is used in each scene of the examination such as a diagnosis, a treatment, or the like. The major factor of the usefulness thereof is that the image includes various explicit and implicit information items and complementary information for complementing the information from a plurality of images can be obtained. For example, a pixel value of the X-ray CT image, a so-called CT value is obtained by imaging X-ray absorption characteristics of a living body, and the value can be recognized by comparing other physical property value of the living body. In addition, the images obtained from the X-ray CT apparatus and the PET apparatus are called a foam image and a functional image, respectively. Since, just as their name says, in the CT image, the shape of the living body is clear, and with respect to this, the PET image can recognize a function of the living body such as a glycometabolism or an amino-acid metabolism, it is possible to medical determine using the information between the CT image and the PET image. For effectively using the medical images in the examination, in PTL 1, a method for constructing a three-dimensional bio data model for a surgical simulation is proposed.

CITATION LIST

Patent Literature

PTL 1: JP-A-2010-17421

In recent years, graph data models attract attention among a lot of modeling techniques. The graph data model applies a structure formed of a node assembly and an edge assembly. An example of a factor to be frequently used in the graph data model includes that a "thing" of a field that is a target is expressed by the node and a relationship between the "thing" and the "thing" is expressed by the edge thereby the field can be naturally expressed, a transition or a movement of the relationship can be expressed by path tracking on a graph, and the field can be instinctively and easily understand.

SUMMARY OF INVENTION

Technical Problem

As described above, a technique that various three-dimensional medical images of a human body are imaged for diagnosis purposes mainly, information which is useful for diagnosis can be acquired from the three-dimensional image through an image processing algorithm and information which is effective for the treatment can also be acquired and the information obtained from the three-dimensional image or information which can be considered from the image is effectively used in the diagnosis and the treatment, has spread widely.

In order to implement the techniques, the current medical image system is generally constructed using a picture archive communication system (PACS) for saving images mainly, a work station (WS) for executing an image process dedicated to, for example, extract an image of a blood vessel of a heart or analysis a brain function, or a treatment plan apparatus for implementing a dose computation as a treatment plan in a case of a radiation treatment, and a digital imaging and communication in medicine (DICOM) standard that is a standard for network connecting between these apparatuses.

Each of apparatuses is connected to each other through the network. For example, a part of the information viewed using a PACS viewer is saved in the PACS. On the other hand, a part of a quantitative value obtained by image processing on the WS is saved in the PACS. However, all of the information is not necessarily transmitted to the PACS and a part of the information is saved in the WS. In addition, in an image obtained by positioning a plurality of images which is obtained by imaging the same patient by the image processing algorithm of the WS or the extracted result, a result obtained through the positioning by the algorithm of the treatment plan apparatus at a time of the treatment planning, when the algorithms are different, the results are not necessarily coincide to each other in some cases. In addition, it is possible to share the result of the positioning which is performed in the WS in the treatment plan apparatus. However, in order to share the result, it is necessary to an effort that the result is transmitted to the PACS once by the DICOM communication and then received in the treatment plan image apparatus.

In the conventional system which is configured by the apparatus dispersed such a manner, in order to effectively utilize the image or the information obtained from the image in each of the medical examination and treatment processes, there are following problems.

(1) A case where image processing algorithms which are performed in the different apparatuses are not common, and the algorithm cannot be executed by sharing the algorithms or a processing procedure which is obtained by combining a plurality of algorithms (hereinafter, referred to as a processing flow) and a parameter thereof, can be assumed.

(2) A case where all of the information items such as a region extracted by the image processing or the processing flow and a quantitative value are saved, and the information cannot be managed including the relationship between the information items can be assumed.

(3) A case where in the same patient or the different patients, the information items extracted by the image processing cannot be temporally and spatially compared can be assumed.

Regarding the problem (1), a system for aiding the diagnosis such as the CAD system as described above is provided. However, the system is currently used as a system dedicated to a lung cancer or a breast cancer. Since there is a plurality of the information items obtained from the image to be obtained in the medical field such as a body part, a blood vessel, or a site of a disease, a system which is capable of using for more general purposes has been desired without the system dedicated to the specific disease. In addition, in the general system, there is a case where for example, in order to implement an extraction or a quantification of a plurality of interested regions in the image, it is difficult to implement by only one image processing algorithm. Accordingly, the information is generally obtained by combining a plurality of algorithms. In the above-described dedicated system, there is a case where it is difficult to execute the processing flow which is arbitrarily combined. Additionally, it is assumed a case where the process or the processing flow cannot be shared between the different apparatuses.

Next, regarding the problem (2), a medical interested region such as a body part, a blood vessel, or a disease is extracted by the image processing or the process flow which is obtained by combining the image processes and the quantitative value such as a size of the disease site is calculated with relation to the extracted region. A part of the information items is added to the image and is saved in the PACS based on the DICOM standard depending on the apparatus. However, it is limited by the designation of the operator. It is not necessarily mean that all of the information items are stored. Furthermore, these information items are generally remained to be saved as a text.

In addition, in a case where the body part, the blood vessel, and the disease are extracted from the same image, in order to save so-called anatomical information indicating that the disease exists in which position of the body part or the disease exists in which position which closer to which blood vessel and the relationships therebetween, it is required to a remarkable effort for saving the information as the text as described above. In the same manner, for example, even in a case where the same diseases are extracted from the two images of a form image and a functional image to obtain a range of entire the disease from the form image and a range with high activity in the disease from the function image, a case where it is difficult to save the relationships therebetween as the text is assumed.

An example of one factor that the information obtained from a single image or a plurality of images cannot be saved and managed includes that a data format (model) for storing these information items is not necessarily clear. With respect to these problems, PTL 1 described above discloses a method and an apparatus for creating a three-dimensional living body data model by applying a physical value of a living body portion by the image information is given using medical image data and separating a target body part from the image data, in order to create data which has a patient specific internal structure and which is capable of biomechanical simulating, along with a surgery simulator development. Specifically, with respect to the CT image and MRI image of the medical image data, the three-dimensional living body data model which is separated into finite elements is created by implementing a distortion correction as an image process and segmentation and further applying the physical value of the position from the corresponding positions of the CT image and the MRI image with respect to each segment. In PTL 1, a method for creating a model in which the physical information (Young's modulus, Poisson's ratio, or the like) is assembled to the segment by implementing the image processes such as a registration and segmentation is disclosed with respect to the medical image. However, there is no description that information items relating to the disease are assembled. In addition, the data model in PTL 1 is a data model aimed at a patient specific surgical simulation. There is no description for a method for comparing models between the plurality of patients and statistical processing.

Next, regarding the problem (3), as described above, since the data model which stores the information extracted by the image processing is not clear in the first place, it cannot be considered that the information is sufficiently saved and accumulated. Even when a part of the information is saved, in order to perform a temporal comparison such as a comparison of the disease information items obtained from the images which are obtained by imaging the same patient at the different time, and to perform a spatial comparison such as a comparison of the anatomical same sites of the body part obtained from the images which are obtained by imaging the different patients, today, a doctor acquires the information items from the dispersed apparatuses and adopts a response.

According to the above-described problems (1) to (3), information from the medical image data cannot be sufficiently and effectively utilized in medical examination and treatment processes.

Therefore, in view of the above features, an object of the present invention is to correlate information, to be processed, about an organ and/or a disease, etc., obtained from a medical image and anatomical/functional medical knowledge information, and enable the information obtained from the medial image to be effectively utilized in medical examination and treatment processes.

Solution to Problem

According to a first aspect of the present invention, there is provided a medical image information system including: a medical knowledge database in which anatomic compartments or functional compartments with respect to organs are stored; a storage unit which stores a graph data model; a display unit which displays the graph data model; and a processing unit, in which the processing unit extracts an organ region and a tract region in the organ from an image to be processed, divides the extracted tract region into a tract node and a tract edge to create a tract graph data model, correlates each region which is obtained by dividing the extracted organ region according to the tract region to the tract graph data model to link between organ region compartment nodes by organ region compartment edge and to create a body part region compartment graph data model, links between functional compartment nodes by functional compartment edges based on the anatomic compartments or the functional compartments of the organ region stored in the medical knowledge database to create an anatomical/functional graph data model, correlates the tract graph data model and/or the organ region compartment graph data model and the anatomical/functional graph data model to create the integrated graph data model, and saves and/or displays the tract graph data model, the organ region compartment data model, the anatomical/functional data model, and/or the integrated graph data model to the storage unit and/or display unit.

According to a second aspect of the present invention, there is provided a medical image information processing method including: extracting an organ region and a tract region in an organ from an image to be processed; dividing the extracted tract region into a tract node and a tract edge to create a tract graph data model; correlating each region which is obtained by dividing the extracted organ region according to the tract region to the tract graph data model to link between organ region compartment nodes by organ region compartment edge and to create a body part region compartment graph data model; linking between functional compartment nodes by functional compartment edges based on the anatomic compartments or the functional compartments of the organ region stored in the medical knowledge database which stores the anatomical compartments or the functional compartments for the organ to create an anatomical/functional graph data model; correlating the tract graph data model and/or the organ region compartment graph data model and the anatomical/functional graph data model to create the integrated graph data model; and saving and/or displaying the tract graph data model, the organ region compartment data model, the anatomical/functional data model, and/or the integrated graph data model to the storage unit and/or display unit.

According to a third aspect of the present invention, there is provided a medical image information processing program for causing a computer to execute: a step of extracting an organ region and a tract region in an organ from an image to be processed by a processing unit; a step of dividing the extracted tract region into a tract node and a tract edge to create a tract graph data model by the processing unit; a step of correlating each region which is obtained by dividing the extracted organ region according to the tract region to the tract graph data model to link between organ region compartment nodes by organ region compartment edge and to create a body part region compartment graph data model by the processing unit; a step of linking between functional compartment nodes by functional compartment edges based on the anatomic compartments or the functional compartments of the organ region stored in the medical knowledge database which stores the anatomical compartments or the functional compartments for the organ to create an anatomical/functional graph data model by the processing unit; a step of correlating the tract graph data model and/or the organ region compartment graph data model and the anatomical/functional graph data model to create the integrated graph data model by the processing unit; and a step of saving and/or displaying the tract graph data model, the organ region compartment data model, the anatomical/functional data model, and/or the integrated graph data model to the storage unit and/or display unit by the processing unit.

Advantageous Effects of Invention

According to the present invention, the present invention which is capable of correlating information, to be processed, about an organ and/or a disease, etc., obtained from a medical image and anatomical/functional medical knowledge information, and enables the information obtained from the medical image to be effectively utilized in medical examination and treatment processes.

BRIEF DESCRIPTION OF DRAWINGS

FIG. 1 is a schematic view illustrating an example of a configuration of an embodiment of a medical image information system according to the present invention.

FIG. 2 is a diagram illustrating an example of a flow of a process in the embodiment of the medical image information system according to the present invention.

FIG. 3 is a diagram illustrating an example of a flow of an image processing/image processing flow in the embodiment of the medical image information system according to the present invention.

FIG. 4 is a diagram illustrating an example of a creation of a graph data model based on the image processing/image processing flow in the embodiment of the medical image information system according to the present invention.

FIG. 5 is a diagram illustrating an example of the graph data model based on anatomical medical knowledge in the embodiment of the medical image information system according to the present invention.

FIG. 6 is a diagram illustrating an example of a method for comparing and creating the graph data model and anatomical graph data model in the embodiment of the medical image information system according to the present invention.

FIG. 7 is a diagram illustrating an outline of an integrated graph data model in the embodiment of the medical image information system according to the present invention.

FIG. 8 is a diagram illustrating an outline of a comparison of the integrated graph data models in the embodiment of the medical image information system according to the present invention.

FIG. 9 is a diagram illustrating an example of a screen for displaying a graph data model of a medical image information treatment system of the present invention.

FIG. 10 is a schematic diagram illustrating an example of a configuration of the embodiment using graph data in the embodiment of the medical image information system according to the present invention.

FIG. 11 is a diagram illustrating an example of a flow of a statistical process of the graph data in the embodiment of the medical image information system according to the present invention.

FIG. 12 is a diagram illustrating an example of a flow of machine learning of the graph data in the embodiment of the medical image information system according to the present invention.

FIG. 13 is a diagram illustrating a process outline of the machine learning of the graph data in the embodiment of the medical image information system according to the present invention.

DESCRIPTION OF EMBODIMENTS

A. Outline

In the present embodiment can provide a medical image information system that is a medical image information system including an image processing unit which is connected to an image server in which a medical image is stored and accumulated through a network, which acquires an image from the image server and performs image processing; a graph data model creating unit for creating a graph data model having a graph structure from information obtained from the image; an anatomical/functional medical knowledge database for saving and accumulating anatomical/functional medical knowledge; a graph data model processing unit including a comparison unit for comparing the graph data model and a graph data model of a graph structure based on the anatomical/functional medical knowledge and an integration unit for integrating the compared graph data models; a graph data storage unit for storing an integrated graph data model; a display processing unit for processing the graph data model for a display purpose; a display unit for displaying the graph data model and an input unit for input an instrument of an operator.

According to the embodiment of the present invention, there is provided a medical image information system including an image processing unit for extracting information to be processed such as an organ or a disease from a medical image, a medical knowledge database for saving anatomical/functional medical knowledge, a graph data model creation unit for exchanging the extracted image information to graph structure type data, a graph data storage unit for storing the data, a comparison unit for comparing the data items, an integration unit for integrating the data, a display unit for displaying the recoded data, in which the image processing unit acquires information from the image obtained from a medical image diagnosis apparatus, the graph data model creation unit exchanges the information to the stored graph structure type data, the comparison unit compares the graph structure type data items of the anatomical/functional medical knowledge, the integration unit creates integrated graph structure type data which is obtained by integrating the graph structure type data items, or the display unit displays the integrated graph structure type data.

In addition, according to the present embodiment, there is provided a data model creation method in the medical image information system, in which the medical image information system includes an image processing unit for extracting information to be processed such as a body part or a disease from a medical image, a medical knowledge database for saving anatomical/functional medical knowledge, a graph data model creation unit for exchanging the extracted information to graph structure type data, and a display unit for displaying the recorded data, in which the graph data model creation unit creates graph structure type data in which a correlation relationship from the medical image is applied based on a process procedure of the image processing unit and the medical knowledge database.

B. Embodiment

Hereinafter, an embodiment of a medical image information system according to the present invention will be described with reference to the drawings.

FIG. 1 is a schematic view illustrating an example of a configuration of an embodiment of a medical image information system according to the present invention. A medical image information system 101 includes an image server 102. The medical image information system 101 is connected to the image server 102 through a network.

The image server 102 stores various medical images, for example, a CT image, an MRI image, a PET image, and an ultrasonic image. The communication or the storage of these images and information items through the network can be easily implemented using, for example, a DICOM format which is commonly used in a medical field.

The medical image information system 101 includes a processing unit 150, an anatomical/functional medical knowledge database (DB) 105 for saving and accumulating anatomical/functional medical knowledge, a graph data storage unit 109 for storing integrated graph data models, a display unit 111 for displaying a graph data model, and an input unit 112 for input an instrument of an operator.

The processing unit 150 includes an image processing unit 103 for acquiring an image from an image server to perform image processing, a graph data model creation unit 104 for creating the graph data model of the graph structure from information obtained from the image, a graph data model processing unit 106 including a comparison unit 107 for comparing the graph data model and the graph data model of a graph structure based on anatomical/functional medical knowledge and an integration unit 108 for integrating the compared graph data models, and a display processing unit 110 for processing the graph data model for a display purpose.

The input unit 112 is means for applying an instrument through a user interface displayed on the display unit 111 to the medical image information system 101 and generally includes a key board, a mouse, or the like. In addition, as the user interface, a graphical user interface (GUI) is generally used.

The display unit 111 displays the graph data model saved in the graph data storage unit 109 and provides information in the graph data model (details will be described later) to a medical staff or the like, thereby facilitating access to the information.

FIG. 2 is a diagram illustrating an example of a flow of a process in the embodiment of the medical image information system according to the present invention.

In FIG. 2, first, in the medical image information system 101, an image to be processed is read through a network from the image server 102 by the image processing unit 103 (Step 201).

The image to be processed is imaged by a three-dimensional tomography apparatus or other image apparatuses such as CT, MRI, and PET, in advance, and stored in the image server 102.

In the image processing unit 103, an image process or an image processing flow which is acquired by combining a plurality of image processes is executed with respect to the obtained image (Step 202).

FIG. 3 is a diagram illustrating an example of a flow of an image processing/image processing flow in the embodiment of the medical image information system according to the present invention.

In the image processing unit 103, as an example of the image process flow, a process corresponding to a liver and a liver neoplasm in a three-dimensional image of an abdomen will be described with reference to FIG. 3.

First, the image processing unit 103 extracts a liver region by an image processing algorithm for performing a region extraction (Step 301). The image processing algorithm for extracting the liver can be executed by an arbitrary image processing algorithm such as a generally well known, that is, a level set method, a graph cut method.

Next, the image processing unit 103 extracts a blood vessel in the liver by the image processing algorithm for performing the region extraction (Step 302). The image processing algorithm for extracting the blood vessel can be executed by an arbitrary image processing algorithm such as a generally well known region growing method.

The image processing unit 103 executes a process for dividing the blood vessel extracted in Step 302 (Step 303). First, the image processing unit 103 confirms a branch from the region extracted in Step 302. Since the method for identifying the branch can determine that a site where a new seed is generated is a branch in a paint routine in a seed-fill algorithm using the region growing method which is used when extracting the above-described blood vessel, for example, the branch can be easily recognized from the extracted result. Since entire the blood vessel is a combination of the branch and blood vessels connecting the branch, the entire the blood vessel can be divided at a boundary of the branch. The blood vessel region is divided as described above.

Next, the image processing unit 103 divides entire the liver which is extracted in Step 301 to a region (Step 304). As an example thereof, in a method which is frequently used in a method for dividing the liver, first, the image processing unit 103 performs thinning processing of the blood vessel which is extracted in Step 302. On the other hand, the result in which the blood vessel which is recognized in Step 303 is divided, the image processing unit 103 extracts a line from a result in which an acral blood vessel, that is, a site that is not between the branch and the branch. Next, the image processing unit 103 can divide the liver region by extracting each region in which a distance between the size and each line is a minimum among the plurality of lines which are subjected to the thinning processing, for the site in the liver region.

Next, the image processing unit 103 extracts a tumor region in the liver by the image processing algorithm for performing the region extraction (Step 305). The image processing algorithm for extracting the tumor can also use a generally well known level set method or the like.

Referring back to FIG. 2, next, the graph data model creation unit 104 creates a graph data model 1 based on the image process or the image processing flow (Step 203).

FIG. 4 is a diagram illustrating an example of a creation of a graph data model based on the image processing/image processing flow in the embodiment of the medical image information system according to the present invention.

A procedure for creating the graph data model will be described with reference to FIG. 4.

First, with respect to the result in which the blood vessel region of Step 303 is divided, since entire the blood vessel is divided into the branch and the blood vessel, the graph data model creation unit 104 creates the branch as a node. The blood vessel start size is set as a special start node. Next, the graph data model creation unit 104 creates a peripheral blood vessel as a node. Next, the graph data model creation unit 104 sets the blood vessel between the branches as an edge, and couples between the branch nodes. Since the graph data model creation unit 104 can designate a direction the start node at this time as a starting point, the graph data model creation unit 104 can add these nodes. Since the direction of the edge is identical to a flow of the blood flow, in a case where the blood vessel is an arterial system, a direction can be set a direction from a start node to the branch and in a case of the blood vessel is a venous system, the direction can be set a direction from the branch to the start node. The graph data model creation unit 104 further couples the branch node and a peripheral blood vessel node with edges. As described above, the direction can be designated by the arterial system or the venous system. Next, the graph data model creation unit 104 applies an arbitrary label, in the present embodiment, since there are eight labels, V1 to V8 to blood vessel nodes in the blood vessel graph data model. Further, the graph data model creation unit 104 can add various feature data items such as mask information of the extracted region, or information of a relative position (actual scale distance) of other branch when a first branch is set as a reference. On the other hand, various feature data items such as a direction of the blood flow, a length of the blood vessel (actual scale), or a volume can be added. The blood vessel graph data model can be created as described above.

On the other hand, the graph data model creation unit 104 creates a liver region compartment graph data model based on the blood vessel graph data model relating to a region obtained by the liver region dividing of Step 304. As described above, since the liver region is divided from the peripheral blood vessel, on the liver region graph data model, the blood vessel node can be exchanged to the liver region. With respect to these nodes, the graph data model creation unit 104 adds an arbitrary label, in the present embodiment, S, and R1 to R8. The graph data model creation unit 104 can add the mask information of the extracted region or various feature data items such as a volume and a shape feature amount to the region node. As described above, the liver region compartment graph data model can be created.

Furthermore, relating to the tumor region which is extracted in Step 305, the graph data model creation unit 104 creates a tumor node. The graph data model creation unit 104 can apply various feature data items such as a feature amount (for example, an amount such as a size, a limbic feature, and uniformity in the tumor) obtained from the image by image processing to the node.

As described above, since the images of the liver and the tumor are extracted in the image processing flow, it can be easily considered that in which region of the liver exist and, in which area of liver exist. Therefore, the graph data model creation unit 104 connects the liver area node in which the tumor node and the tumor exist on the graph, that is, can introduce the tumor node to the liver region compartment graph data model.

The number of the graph data model 1 may be a plurality of graph data models as described about without one graph data model. However, since the graph data models are subjected to a process in the same image processing flow, the corresponding nodes or the edges in the graph data models are clear. Accordingly, it is possible to easily correlate therebetween.

Next, the graph data model processing unit 106 acquires the graph data model 2 based on the anatomical/functional medical knowledge from the anatomical/functional medical knowledge database 105 (Step 204).

FIG. 5 is a diagram illustrating an example of the graph data model based on anatomical medical knowledge in the embodiment of the medical image information system according to the present invention.

A graph data model 2 will be described in detail with reference to FIG. 5. The liver that is a target in the present example receives supplying of the blood from two blood vessels, one blood vessel is a hepatic artery which plays a role of a nutrient vessel and another blood vessel is a portal which plays a role of a functional blood vessel. As illustrated in the drawing of a liver area dividing in FIG. 5, an area of lobes of the liver is divided into two of an anatomical compartment and a functional compartment (functional liver area representation). However, in clinical use, the functional compartment is usually used. The reason why the functional compartment is usually used is that in the liver, a blood supply is mainly performed by the portal in the liver. A method for performing a compartment by a portal supply in the liver is mainly used. As illustrated in FIG. 5, the liver is divided into five areas and eight subsegments by the functional compartment. Each node allocates a type of the liver lobes (left lobe and right lobe), areas (C, L, M, A, and P), the subsegments (S1 to S8). It is possible to create the graph data model which connects them. The graph data model processing unit 106 creates the anatomical/functional graph data model as described above.

Next, in the graph data model processing unit 106, the comparison unit 107 compares the graph data model 1 based on the image processing flow and the graph data model 2 based on the anatomical/functional medical knowledge (Step 205) and the integration unit 108 creates the integrated graph data model based on the graph data model 1 and the graph data model 2 (Step 206).

FIG. 6 is a diagram illustrating an example of a method for comparing and creating the graph data model and anatomical graph data model in the embodiment of the medical image information system according to the present invention.

First, a method for comparing the graph data model will be described with reference to FIG. 6. In the present embodiment, the graph data model 1 is a liver region compartment graph data model, and the graph data model 2 is an anatomical/functional graph data model of the liver. As illustrated in FIG. 6, it is considered that the two data items are different to each other. However, as a feature of the graph structure, the shape can be changed while maintaining the relationship between the node and the edge. Accordingly, the comparison unit 107 changes the graph data model 2 as illustrated in FIG. 6, and can correlate the nodes and the edges of the graph data models by comparing the shapes, that is, so-called graph matching. The procedure will be described in below.

First, since the comparison unit 107 and the graph data models 1 and 2 have a graph structure, it is possible to find the corresponding node by comparing the graph node orders, that is, the shapes of the graphs from the characteristics of the graph structure. Accordingly, the comparison unit 107 can easily change the graph data model 2 as illustrated in FIG. 6. In FIG. 6, the comparison unit 107 can find the corresponding node up to a start node S and a branch node of the graph data model 1. However, since there is a case where the region nodes of the graph data model 1 cannot be correlated by only the graph node orders, next, the comparison unit 107 compares data items stored in the nodes and the edges. For example, the comparison unit 107 stores the feature data items such as a length of the blood vessel, a volume of the blood vessel, or the like to each edges, and stores the feature data items such as the volume of the liver compartment, a shape feature amount, or the like to the node. Accordingly, by comparing the values, it is possible to correlate the nodes or the edges in which a closer value is stored, for example.

The volume or the like of the blood vessel or the region can be easily stored in the graph data model 1 that is a result of the image processing. However, since it is required to an additional process for input the data to the anatomical/functional graph data, the details thereof will be described in a section of a usage of the accumulated data to be described below.

As described above, by comparing the graph data model 1 and the graph data model 2, it is possible to correlate the graph data models.

By correlating the graph data models, for example, in the graph data model 1, that is in the liver region compartment data model, arbitrary labels R1 to R8 which are allocated to the nodes of each liver area are the just different labels as a result of the image processing. In the graph data model 2, that is, the anatomical/functional graph data model, it is possible to switch from a classification label S1 to a classification label S8 which are classified depending on the function of the liver area having clinical meaning.

In the present example, an example that labeling is performed to the nodes to add the label having the clinical meaning is described. However, when adding the label having the clinical meaning to each edge of the anatomical/functional graph model in advance, the labeling can be performed to the edge in the same manner of the node.

FIG. 7 is a diagram illustrating an outline of an integrated graph data model in the embodiment of the medical image information system according to the present invention.

Furthermore, a method for creating the integrated graph data model based on the graph data model 1 and the graph data model 2 will be described with reference to FIG. 7. In the present example, as an example thereof, the graph data model 1 is the liver region compartment graph data model and is configured of the branch node of the blood vessel and the liver area node and the connecting edges thereof as described above. In addition, as an example thereof, the graph data model 2 is the anatomical/functional graph data model and is configured of the functional compartment having the clinical meaning and the connecting edges thereof. In addition, as described above, the corresponding relationship is clear by comparing between the graph data models. Accordingly, the integration unit 108 can create the integrated graph data model which is formed of the blood vessel node, the liver region compartment node based on the anatomical/functional graph data model, and the tumor node, and the connecting edges, based on the corresponding relationship. The tumor node saves a clinical data master or an image data master as described above, and the blood vessel branch node saves a branch position data master which uses a first branch as a reference as described above. As described above, the integration unit 108 creates the integrated graph data model.

In addition, in the present example, the integrated graph data model having the above-described configuration is constructed. However, the configuration can be changed depending on the purpose. In addition, it is possible to create a plurality of graph data models without one graph data model.

The graph data model processing unit 106 saves a created integrated graph data model 1 in the graph data storage unit 109 (Step 207).

The graph data model processing unit 106 may save any one of the blood vessel graph data model, the liver region compartment graph data model, and the anatomical/functional graph data model or the plurality of thereof in addition to the integrated graph data model to the graph data storage unit 109. In addition, the saving timing is not limited to Step 207, and can be set at the appropriate timing. In addition, when each graph data model is saved, in order to classify the graph data model, appropriate classification information such as a patient, a body part, a disease, or the like is added and saved.

Next, a method for comparing the image data items imaged in the same patient at the different time will be described in detail.

First, the display processing unit 110 acquires the past integrated graph data model 0 in the same patent by the graph data storage unit 109 with respect to the above described integrated graph data model 1 (Step 208) and compares the two integrated graph data models (Step 209).

FIG. 8 illustrates a date example which is stored in the integrated graph data model. When focusing the tumor nodes, in each tumor node, the storing data master exists, and the clinical data or the image data is stored. Regarding each of the tumor nodes, in this example, T0 exists in a liver area S5 at a time t0, and T1-2 exists in S5 and T1-1 exists in S7 at a time t1. That is, the number of tumors increases between t0 to t1. However, in the present embodiment, since there is a graph structure which is obtained by combining each of the tumor nodes at the liver area, the tumors T0 and T1-2 can be easily compared. Accordingly, it can be considered that T1-1 is a new tumor.

The display processing unit 110 displays the comparing result to the display unit 111 (Step 210).

FIG. 9 illustrates an example of comparison results of the integrated graph data model. As a feature of the graph, since the graph can be intuitively and easily understood, it is possible to display the integrated graph data model 0 and the integrated graph data model 1 without any change. In addition, when a lot of tracking is performed by the input unit 112, by clicking the tumor T0 with a mouse pointer, the display processing unit 110 can display the information included in the node. Since it is easily understood that the tumor corresponding to the tumor T0 is T1-2 as described above from the graph structure, by only clicking the node of the tumor T0, the change amount as illustrated in FIG. 9 can be easily displayed. The operator as described above can easily access the integrated graph data model and the comparing of the data items can be easily performed.

The display processing unit 110 may store the comparing result and the classification information for specifying the comparing result to the graph data storage unit 109.

An example in which only the integrated graph data model is displayed is illustrated in FIG. 9. The integrated graph data model and the image used in the creation may be displayed side by side or may be displayed by overlapping the volume rendering image of the image. In addition, a plurality of graph data models may be displayed at three or more times.

(Use of Graph Data)

A method for using the accumulated graph data items in the embodiment of the medical image information system of the present invention will be described with reference to FIGS. 10 to 13. Here, an example in which the anatomical/functional medical knowledge graph data model is updated mainly using the accumulated graph data items and the above-described graph matching can be executed with higher accuracy is described.

FIG. 10 is a diagram illustrating an example of a configuration using accumulated graph data in the embodiment of the medical image system according to the present invention. A medical image information system 101 includes a graph data processing unit 1001 and the graph data processing unit 1001 includes a statistical processing unit 1002 and/or a graph data machine learning unit 1003.

(Improvement in Comparison Accuracy of Graph Data Model by Statistical Processing of Accumulated Graph Data)

FIG. 11 is a diagram illustrating a sequence using of a flow of statistical processing and using of the accumulated graph data in the embodiment of the medical image information system according to the present invention.

In FIG. 11, first, in the medical image information system 101, the statistical processing unit 1002 of the graph data processing unit 1001 acquires a plurality of graph data items in the same model (for example, a specific body part such as a liver, a specific disease of the specific body part, or the like) by the graph data storage unit 109 (Step 1101). The statistical processing unit 1002 acquires the data stored in the focusing same nodes or the edges from the obtained plurality of graph data items (Step 1102). Since the data items are in the same model, the data can be easily obtained from the liver area node S1 as the above described example, for example. The statistical processing unit 1002 performs the statistical processing to the statistical processing unit 1002 with respect to the statistical data of the nodes and/or the edges acquired from the plurality of graph data items, and calculates the statistical data such as an average value, a dispersion value, a maximum value, and a minimum value of the feature data items (Step 1103). The statistical processing unit 1002 stores theses statistical data items to the anatomical/functional medical knowledge DB 105 in the anatomical/functional medical knowledge DB 105 corresponding to the node and/or the edge (Step 1104). The statistical data obtained here is a so-called statistical model which is created from a plurality of data items. For example, an average value of the volumes of the above-described liver area nodes is stored. When graph matching of the anatomical/functional medical knowledge graph data model and the graph data model which is created by the image processing, the statistical processing unit 1002 compares the values, and matches the nodes and/or the edges which have closer value. Accordingly, it is possible to improve the matching accuracy.

(Improvement in Comparison Accuracy by Machine Learning of Accumulated Graph Data and Updating Graph Data Model Comparison Unit)

FIG. 12 is a diagram illustrating a procedure using machine learning of the accumulated graph data in the embodiment of the medical image information system according to the present invention.

In FIG. 12, first, in the medical image information system 101, a graph data machine learning unit 1003 of the graph data processing unit 1001 acquires a plurality of graph data items in the same model (for example, a specific body part such as the liver, a specific disease of the specific body part) by the graph data storage unit 109 (Step 1201). The graph data machine learning unit 1003 acquires focusing feature data stored in the same nodes or edges from the acquired plurality of graph data items (Step 1202). The graph data machine learning unit 1003 performs machine learning to the graph data machine learning unit 1003 of the graph data processing unit 1001 using the feature data which is stored in the acquired nodes or edges (Step 1203).

The several machine learnings in Step 1203 are proposed. However, hereinafter, as an example thereof, the machine learning will be described using an adaboost algorithm that is one method of the machine learning. The graph data machine learning unit 1003 may use other machine learning and an appropriate learning method such as a neural network.

In generally, in the leaning by the adaboost, the different classifier that is referred to as a weak classifier is made by sequentially changing the weight of a leaning sample and a strong classifier is obtained by combining the weak classifiers. Simply, the method is a method for sequentially leaning the weak classifier, that is, a method for improving the accuracy by chaining the weight.

A strong classifier Ht(x), which is obtained by leaning from T weak classifiers ht(x) with respect to an input pattern x, is represented by Expression (1) below.

$$H(x) = \text{sign}\left[\sum_{t=1}^{T} \alpha_t h_t(x)\right] \text{ Where,} \quad \text{[Expression 1]}$$

αt: reliability

T: the number of classifiers

Where, αt represents a reliability and T represents the number of classifiers.

In this manner, the strong classifier is configured by weighting and combining T weak classifiers ht(x) with the reliability αt.

In addition, the weak classifier ht(x) is generally designed by Expression (2) below.

$$h(t) = \begin{cases} 1 & \text{if } pz(x) > p\theta \\ -1 & \text{otherwise} \end{cases} \text{ Where,} \quad \text{[Expression 2]}$$

z: reference value of certain storage value p: parity indicating direction of symbol θ: threshold value Where, z(x) represents a reference value of a certain numerical value, p represents a parity indicating a direction of a symbol, and θ represents a threshold value.

In a case where a certain numeric value is greater than a set threshold value, that is, a case where the classification can be performed, the weak classifier ht(x) is a function that returns 1, and in a case where the certain numeric value is smaller than the threshold value, that is, the classification cannot be performed, the weak classifier ht(x) is a function that returns −1. The direction of the symbol can be changed by the parity and a reverse case (the certain value is smaller than the threshold value) can be established.

In the present embodiment, the weak classifier is designed by the focusing numerical value (storage amount) stored in the nodes and edges and the strong classifier is created from the weak classifiers. The details thereof will be described below with reference to the drawings.

FIG. 13 is a diagram illustrating a process outline of the machine learning of the graph data in the embodiment of the medical image information system according to the present invention.

Here, a status where N graph data items acquired from the graph database exist, that is, N learning samples are corrected is considered.

As described above, examples of the storage amount of the node or the edge include a volume of the blood vessel, a length of the blood vessel, a volume of the liver area, or the like. Here, it is assume that there are T storage amounts described above, and one of the storage amount among them is set to z.

Since there are N graph data items acquired in Step 1202, a threshold value θ relating to the storage amount of the focusing node is obtained. In a case where the rate for satisfying the value θ is high, the reliability αt is increased, and the reliability αt of the weak classifier indicated by the feature amount is increased. By repeating T weak classifier, reliability αt of each weak classifier is updated.

A majority decision is performed by weighing the weak classifier obtained such a manner at the reliability αt as illustrated in FIG. 13 to obtain a strong classifier Ht(x).

Next, a method for obtaining the reliability αt will be described.

Learning procedures in a case where M leaning sample (feature amount) is given will be shown in below.

First, a weight Dt (t=1, . . . , T (T indicates the number of weak classifiers)) of each sample is initialized by Dt=1/M evenly over all of the samples.

Since the sample saves any information of "correct" or "error" (correct data or incorrect data), an error rate εt for the sample to the sum of the weights of the error samples is calculated by Expression (3) below.

$$\varepsilon_t = \sum_{i: y_i \neq h_t(x_i)} D_t(i) \text{ Where,} \quad \text{[Expression 3]}$$

i: sample number

Dt: weight of sample yi = +1(detection target) or

− 1(non-detection target)

Where, i represents a sample number and Dt represents a sample weight.

For example, when classifying two classes, the error rate εt is 0.5 even when the classes are appropriately allocated. By using the error rate, the reliability αt is obtained by Expression (4) below.

$$\alpha_t = \frac{1}{2}\log\left(\frac{1-\varepsilon_t}{\varepsilon_t}\right) \text{ Where,} \quad \text{[Expression 4]}$$

εt: error rate

That is, the value of the reliability αt becomes smaller as the error rate is increased. On the contrary, the value of the reliability αt becomes larger as the error rate is decreased.

Next, the weight Dt of the sample is updated by Expression (5) below.

$$D_{t+1}(i) = D_t(i)\exp[-\alpha_t y_i h_t(-\alpha_t)] \quad \text{[Expression 5]}$$

Where, i: sample number

Dt: weight of sample yi=+1 (detection target) or
−1 (non-detection target)

The weight of the sample which can be accurately classified by the weak classifier becomes smaller, and the weight of the wrong sample becomes lager.

By repeating these procedures relating to T weak classifiers, the reliability αt with respect to the leaning sample can be obtained.

By machine learning for a storage amount stored in the graph data as described above, the feature storage amount having a focusing region or blood vessel in the node or the edge is obtained and the strong classifier for classifying the storage amounts can be created.

The procedures is repeated by the graph data machine learning unit 1003 relating to each node and edge in the graph data model, and each strong classifier is created.

The graph data machine learning unit 1003 stores the strong classifier which is obtained by machine learning as described above to the anatomical/functional medical knowledge graph data model and saves them to the anatomical/functional medical knowledge database 105 (Step 1204).

According to the above-described flows, when comparing the anatomical/functional graph data model and the graph data model obtained from the image, it is possible to perform graph matching with higher accuracy such that a numerical value that is stored in the focusing node or edge of the graph data model obtained from the image is applied to the strong classifier in the node or edge of the anatomical/functional graph data model to classifier that the classifying whether or not the graph data models are consistent with each other.

In the above-described embodiment, the DICOM format is used as the format of the image (data format) however, other formats such as a JPEG image and a bitmap image may be used.

Further, the configuration where the image server 102 saves data files is used; however, the medical image information system 101 and the graph data model creation unit 104 may directly communicate with each other to exchange a data file.

While the configuration where communication of a data file or the like through the network is used has been described, other storage media, for example, large-capacity storage media such as a flexible disk and a CD-R, may be used as means that exchanges a data file.

According to the present embodiment, the medical image information system, the medical image information processing method, and the program which is capable of extracting information to be processed such as an organ or a disease from the medical image by the image process/image processing flow, creating the graph data model of the information, and comparing the graph data models (furthermore, capable of statistical processing and/or learning processing).

Specifically, in the present embodiment, the image process or the image processing flow which is obtained by combining various image processes can be executed, thereby various information items required for the examination can be acquired.

In addition, by providing the data model which is characterized by a graph structure for storing the information obtained by the image processing flow and the anatomical/functional medical knowledge, the obtained information items can be correctively saved. Specifically, the integrated graph data model which is obtained by comparing the information which is obtained from the image and the anatomical/functional medical knowledge and by combining these information items can be provided.

Furthermore, by providing a result which is obtained by comparing data items at the different time of the same patient using the integrated graph data model, and by machine learning relating to disease at the same site of the difference patents, a new data model can be provided for a treatment strategy or a treatment plan.

The present invention and the present embodiment can be applied to the appropriate organ such a stomach, a heart, a pancreas, a kidney, a prostate, a colon, a gall bladder, a brain, a lung, a spleen, a muscle, the other body parts, or an assembly of the body parts in addition to the liver. Further, the present invention and the present embodiment can be applied to a lymph vessel (including a lymph node), a bone, a nerve, a trachea, a bile duct, a urethra, or the other tracts, in addition to the blood vessel. The present invention and the present embodiment can be applied to the appropriate disease such as a thrombus in addition to the tumor.

The present invention is not always restricted to the embodiments described above but includes various modification embodiments. For example, the previously shown embodiments have been described specifically for easy explanation of the present invention and the invention is not always restricted to those having all of such configurations. Further, a portion of the configuration of an embodiment can be replaced with the configuration of other embodiments, or a configuration of an embodiment can be incorporated with the configuration of other embodiments. Further, other configuration may be added to, deleted from, or replaced with part of configuration of respective embodiments.

Further, each of the configurations, functions, processing sections, processing units, or the like described above may be partially or entirely realized in hardware, for example, by designing them by an integrated circuit. Further, each of the configurations, functions, etc. described above may also be realized by software in which a processor interprets a program for realizing respective functions and executing them. Information such as in program, table, file, etc. for realizing each of the functions may be provided in a recording device such as a memory, hard disk, or SSD (Solid State Drive), or may be provided in a recording medium such as IC card, SD card, or DVD.

Further, control lines and information lines which are considered necessary in view of explanation are shown, and all of control lines and information lines are not always shown in view of products. It may be considered that substantially all of the configurations are actually connected to each other.

The medical image information system and medical image information processing method according to the present invention can be provided by a medical image information processing program for causing a computer to execute each procedure, a computer readable recording medium that records the medical image information processing program, a program product that includes the medical image information processing program and may be loaded into an internal memory of the computer, a computer such as a server including the program.

REFERENCE SIGNS LIST

101 . . . medical image information system
102 . . . image server
103 . . . image-processing unit
104 . . . graph data model creation unit
105 . . . anatomical/functional medical knowledge database
106 . . . graph data model processing unit 107 . . . graph data model comparison unit
108 . . . graph data model integration unit
109 . . . graph data storage unit
110 . . . display processing unit
111 . . . display unit
112 . . . input unit
1001 . . . graph data processing unit
1002 . . . graph data statistical processing unit
1003 . . . graph data machine learning unit

The invention claimed is:

1. A medical image information system comprising:
a medical knowledge database in which predetermined anatomic compartments or predetermined functional compartments with respect to one or more organ models are stored;
a storage medium storing instructions;
a display device; and
a processor connected to the storage medium, the display device and the medical knowledge database,
wherein the processor, when executing the instructions stored in the storage medium, is configured to:
extract an organ region and a tract region in the organ region from an image to be processed which contains an imaged organ,
divide the extracted tract region into a plurality of tract nodes linked by a plurality of tract edges to create a tract graph data model,
divide the extracted organ region according to the extracted tract region and the tract graph data model into a plurality of organ region compartment nodes linked by a plurality of organ region compartment edges to create an organ region compartment graph data model,
acquire an anatomical/functional graph data model which includes a plurality of functional compartment nodes linked by a plurality of functional compartment edges based on the anatomic compartments or the functional compartments of the one of the organ models stored in the medical knowledge database corresponding to the imaged organ,
correlate at least one of the tract graph data model and the organ region compartment graph data model with the anatomical/functional graph data model to create an integrated graph data model, and
display at least one of the tract graph data model, the organ region compartment data model, and the anatomical/functional data model with the integrated graph data model on the display device.

2. The medical image information system according to claim 1,
wherein the processor, when executing the instructions stored in the storage medium, is further configured to:
extract a disease region in the organ region to create a disease node, and
link the disease node to the organ region compartment nodes that has a disease on the organ region compartment graph data model, and
correlate the organ region compartment graph data model linked with the disease node with the anatomical/functional graph data model to create an integrated graph data model including the disease node.

3. The medical image information system according to claim 2,
wherein the processor, when executing the instructions stored in the storage medium, is further configured to:
assign a label to the disease node, amply a size, a limbic feature, a uniformity in the disease, or other feature data, and
store the tract graph data model, the organ region compartment data model, the anatomical/functional data model, and the integrated graph data model.

4. The medical image information system according to claim 3,
wherein the processor, when executing the instructions stored in the storage medium, is further configured to:
display at least one of the tract graph data model, the organ region compartment data model, and the anatomic/functional data model with the integrated graph data model with the labelled disease node and feature data of the labelled disease node.

5. The medical image information system according to claim 2,
wherein the imaged organ includes at least one of a liver, a stomach, a heart, a pancreas, a kidney, a prostate, a colon, a gall bladder, a brain, a lung, a spleen, an a muscle,
the tract region includes at least one of a plurality of blood vessels, a plurality of lymph vessels, a trachea, a bile duct, and an urethra, and
the disease includes a tumor or a blood clot.

6. The medical image information system according to claim 1,
wherein the processor, when executing the instructions stored in the storage medium, is further configured to:
add at least one of mask information of the extracted tract region or information of relative positions of the tract nodes, to the tract graph data model, or
add at least one of flow directions, lengths or volumes of the tract edges to the tract graph data model, or
add at least one of mask information of the extracted organ region, volumes, or shape feature amounts of the organ region compartment nodes the organ region compartment graph data model.

7. The medical image information system according to claim 6,
wherein the at least one of the tract graph data model and the organ region compartment graph data model is correlated with the anatomical/functional graph data model based on values of the tract nodes, the tract edges, the organ region compartment nodes, the organ region compartment edges, the functional compartment nodes and the functional compartment edges.

8. The medical image information system according to claim 6,
wherein the at least one of the tract graph data model and the organ region compartment graph data model is correlated with the anatomical/functional graph data model based statistical processing of values of the tract nodes, the tract edges, the organ region compartment nodes, the organ region compartment edges, the functional compartment nodes and the functional compartment edges.

9. The medical image information system according to claim 6,
wherein the at least one of the tract graph data model and the organ region compartment graph data model is correlated with the anatomical/functional graph data model based a plurality of classifiers and values of the tract nodes, the tract edges, the organ region compartment nodes, the organ region compartment edges, the functional compartment nodes and the functional compartment edges.

10. The medical image information system according to claim 6,
wherein the processor, when executing the instructions stored in the storage medium, is further configured to:
when one of the tract nodes or the organ region nodes is specified, display feature data of the specified node on the display device.

11. The medical image information system according to claim 1,
wherein the processor, when executing the instructions stored in the storage medium, is further configured to:
perform a thinning process on the extracted tract, and
obtain a combination of a site and a line in which a distance between the site and each line is a minimum among the plurality of lines which are subjected to the thinning processing, for the site in the extracted organ region, and extracts each site region which has the same combination to divide the extracted organ region.

12. The medical image information system according to claim 1,
wherein the extracted tract region includes a plurality of tracts and one or more branches thereof,
a tract start site is set as a special start tract node of the tract nodes,
tracts at a periphery are set as the tract nodes,
the branches are set as the tract nodes,
the tracts between the branches are set as the tract edges and link the tract nodes of the branches with the tract nodes of the tracts at the periphery.

13. The medical image information system according to claim 1,
wherein the storage medium further stores a predetermined tract graph data model, a predetermined organ region compartment data model, a predetermined integrated graph data model corresponding to the imaged organ of a same patient, and
the processor, when executing the instructions stored in the storage medium, is further configured to:
compare the predetermined tract graph data model, the predetermined organ region compartment data model and the predetermined integrated graph data model with the created tract graph model, the created organ region compartment data model and the created integrated graph data model, and
display a result of the comparison on the display device.

14. The medical image information system according to claim 1,
wherein the processor, when executing the instructions stored in the storage medium, is further configured to:
assign a label to each of the tract nodes, tract edges, the organ region compartment nodes, the organ region compartment edges, the anatomic/functional compartment nodes and, the anatomic/functional compartment edge, and
display at least one of the tract graph data model, the organ region compartment data model, the anatomical/functional data model and the integrated graph data model on the display device with the labels.

15. A medical image information processing method comprising:
extracting an organ region and a tract region in the organ region from an image to be processed which contains an imaged organ;
dividing the extracted tract region into a plurality of tract nodes and a plurality of tract edges to create a tract graph data model;
dividing the extracted organ region according to the extracted tract region and the tract graph data model to into a plurality of organ region compartment nodes linked by a plurality of organ region compartment edges to create an organ region compartment graph data model;
acquiring an anatomical/functional graph data model which includes a plurality of functional compartment nodes linked by a plurality of functional compartment edges based on anatomic compartments or functional compartments of a predetermined organ region corresponding to the imaged organ;
correlating at least one of the tract graph data model and the organ region compartment graph data model with the anatomical/functional graph data model to create an integrated graph data model; and
displaying at least one of the tract graph data model, the organ region compartment data model, and the anatomical/functional data model, with the integrated graph data model.

16. A non-transitory, computer readable medium storing a medical image information processing program for causing a computer to perform acts of:
extracting an organ region and a tract region in the organ region from an image to be processed which contains an imaged organ;
dividing the extracted tract region into a plurality of tract nodes and a plurality of tract edges to create a tract graph data model;
dividing the extracted organ region according to the extracted tract region and the tract graph data model into a plurality of organ region compartment nodes linked by a plurality of organ region compartment edges to create an organ region compartment graph data model;
acquiring an anatomical/functional graph data model which includes a plurality of functional compartment nodes linked by a plurality of functional compartment edges based on anatomic compartments or functional compartments of a predetermined organ region corresponding to the imaged organ;
correlating at least one of the tract graph data model and the organ region compartment graph data model with the anatomical/functional graph data model to create an integrated graph data model; and
displaying at least one of the tract graph data model, the organ region compartment data model, and the anatomical/functional data model, with the integrated graph data model.

* * * * *